United States Patent [19]

Monte et al.

[11] 4,087,402
[45] May 2, 1978

[54] ORGANO-TITANATE CHELATES AND THEIR USES

[75] Inventors: Salvatore J. Monte, Staten Island, N.Y.; Gerald Sugerman, Allendale, N.J.

[73] Assignee: Kenrich Petrochemicals, Inc., Bayonne, N.J.

[21] Appl. No.: 677,980

[22] Filed: Apr. 19, 1976

Related U.S. Application Data

[63] Continuation-in-part of Ser. No. 618,222, Sep. 30, 1975, abandoned.

[51] Int. Cl.$^2$ .................................................. C08K 9/00
[52] U.S. Cl. ........................... 260/42.14; 106/288 B; 106/288 Q; 106/299; 106/300; 106/308 F; 106/308 Q; 260/414; 260/429.5
[58] Field of Search ................... 260/429.5, 42.14; 106/299, 308 Q, 288 B, 288 Q, 300, 308 I, 308 F, 414; 428/407

[56] References Cited

U.S. PATENT DOCUMENTS

| | | | |
|---|---|---|---|
| 2,809,162 | 10/1957 | Lowe | 260/429.5 X |
| 2,898,356 | 8/1959 | Russell | 260/429.5 |
| 2,913,469 | 11/1959 | Russell | 260/429.5 |
| 3,032,570 | 5/1962 | Haslam | 260/429.5 X |
| 3,337,391 | 8/1967 | Clayton et al. | 260/429.5 |
| 3,660,134 | 5/1972 | Morris | 106/308 Q |
| 3,856,839 | 12/1974 | Smith et al. | 260/429.5 |

OTHER PUBLICATIONS

Chemical Abstracts, 53, 2094f, (1959).
Chemical Abstracts, 51, 12961h, (1957).
Chemical Abstracts, 74, 42016t, (1971).
Chemical Abstracts, 15, 129861j, (1971).

*Primary Examiner*—Helen M. S. Sneed
*Attorney, Agent, or Firm*—Bert J. Lewen

[57] ABSTRACT

New chelate compounds which are alpha,omega-alkylene titanates having two non-hydrolyzable groups. The compounds may be represented by the formula:

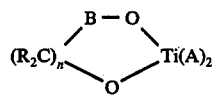

where A represents a non-hydrolyzable group, B is an $R_2C$ group or a carbonyl group, R may be hydrogen or alkyl groups having 1 to 6 carbon atoms and $n$ may be 1 or 2. Preferably R is hydrogen. The R in a particular molecule may be the same or different.

The compounds are particularly useful for treating inorganic fillers which are used to extend or modify the properties of polymeric materials. The compounds maintain high activity even when applied to filler containing free water.

20 Claims, No Drawings

ORGANO-TITANATE CHELATES AND THEIR USES

RELATED APPLICATION

This case is a continuation-in-part of copending U.S. patent application Ser. No. 618,222, filed Sept. 30, 1975, now abandoned.

This invention relates to a new and improved class or organic titanate compounds. More specifically, this invention relates to organic titanate chelates which are particularly useful for treating fine inorganic materials. The treated fillers, in turn, are useful for extending polymeric materials.

Inorganic materials have long been used as fillers, pigments, reinforcements and chemical reactants in polymers. They are essentially hydrophilic, i.e., easily wetted by water and able to absorb water. However, their compatibility with polymers is limited. Therefore, poor utilization is obtained of the potential reinforcement, color or opacity, or chemical reactivity of the organic material.

It has been proposed to employ surface active agents to facilitate the incorporation of these inorganic materials into polymers. However, the known materials have had many shortcomings, such as poor stability in the presence of free water, and limited ability to completely disperse large amounts of the filler materials in the polymeric material.

The present invention results in the formation of a reinforced polymer which has a lower melt viscosity, improved physical properties, and better pigmenting characteristics than that displayed in the prior art.

In order to overcome the aforesaid deficiencies, applicants have discovered a new class of organic titanate compounds. These compounds may be represented by the formula:

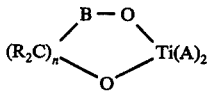

where the Rs are monovalent radicals which may be hydrogen or an alkyl group having from 1 to 6 carbon atoms and where $n$ may be 1 or 2. B is an alkylene group ($R_2C$) or carbonyl. Preferably, the Rs are hydrogen, but they may also be methyl, ethyl or other short chain alkyl groups. The Rs need not be the same in a particular molecule or on each methylene unit.

The monovalent non-hydrolyzable group (A) may be acyl, aryloxy, thioaryloxy, sulfonyl, sulfinyl, diester pyrophosphate and diester phosphate. The aryloxy group may be a substituted or unsubstituted phenoxy or naphthyloxy group containing up to about 60 carbon atoms. It may be substituted by alkyl, alkenyl, aryl, aralkyl, alkaryl, halo, amino, epoxy, ether, thioether, ester, cyano, carbonyl, or aromatic nitro groups. Preferably no more than three substituents per aromatic ring are present. The thioaryloxy groups are substantially the same as the aforesaid aryloxy groups except that the phenolic oxygen is replaced by sulfur. Of the aryloxy and thioaryloxy groups, phenoxy or naphthoxy are preferred. By non-hydrolyzable is meant a group which will not cleave in a neutral aqueous solution at a temperature less than 100° C. Hydrolysis can be determined by analyzing for liberated acids or alcohols.

The acyl, sulfonyl, sulfinyl, diester pyrophosphate and diester phosphate ligand, respectively, are represented by the following formulas:

OCOR', —OSO$_2$R", —OSOR",
(R"O)$_2$P(O)OP(OH)(O)— and (R"O)P(O)O— wherein R" may be the same as R' as defined below. Where A is a sulfonyl or a sulfinyl group, it is preferred that R" be phenyl, a substituted phenyl or an aralkyl group having from 5 to 24 carbon atoms in the alkyl chain. Where A is a phosphate group, it is preferred that the R" group have from 6 to 24 carbon atoms, and where A is a pyrophosphate group, it is preferred that the R" group be alkyl having up to 12 carbon atoms.

In the acyl ligand (OCOR'), the R' may be hydrogen or a monovalent organic group having from 1 to about 100 carbon atoms; particularly, an alkyl, alkenyl, aryl, aralkyl or alkaryl group. The aryl groups may be substituted or unsubstituted phenyl or naphthyl groups, preferably containing up to 60 carbon atoms. Additionally, the R' group may be substituted with halo, amino, epoxy, ether, thioether, ester, cyano, carboxyl and/or aromatic nitro substituents. Generally up to about six substituents may occur per R' group. The R' group may contain intermediate hetero atoms such as sulfur or nitrogen in the main or pendant substituents. R' is preferably a long chain group having 18 carbon atoms. Most desirably, all R's are the same.

Examples of specific R' ligands are: methyl, propyl, cyclopropyl, cyclohexyl, tetraethyloctadecyl, 2,4-dichlorobenzyl, 1-(3-bromo-4-nitro-7-acetylnaphthyl)ethyl, 2-cyano-furyl, 3-thiomethyl-2-ethoxy-1-propyl and methallyl.

Examples of A ligands useful in the practice of this invention include 11-thiopropyl-12-phenyloctadecylsulfonyl, 2-nitrophenylsulfinyl, di(2-omega-chlorooctyl)-phenyl phosphato, diisonicotinyl pyrophosphato, 2-nitro-3-iodo-4-fluorothiophenoxy, 2-methallylphenoxy, phenylsulfinyl, 4-amino-2-brom-7-naphthylsulfonyl, diphenyl pyrophosphato, diethylhexyl pyrophosphato, di-sec-hexylphenyl phosphato, dilauryl phosphato, methylsulfonyl, laurylsulfonyl and 3-methoxynaphthalene sulfinyl. Examples of aryloxy groups are 2,4-dinitro-6-octyl-7-(2-bromo-3-ethoxyphenyl)-1-naphthoyl and 3-cyano-4-methoxy-6-benzoylphenoxy.

Examples of the R' groups are numerous. These include straight chain, branched chain and cyclic alkyl groups such as hexyl, heptyl, octyl, decyl, dodecyl, tetradecyl, pentadecyl, hexadecyl, octadecyl, nonadecyl, eicosyl, docosyl, tetracosyl, cyclohexyl, cycloheptyl, and cyclooctyl. Alkenyl groups include hexenyl, octenyl and dodecenyl.

Halo-substituted groups include bromohexyl, chlorooctadecyl, iodotetradecyl and chlorooctahexenyl. One or more halogen atoms may be present, as for example in difluorohexyl or tetrabromooctyl. Ester-substituted aryl and alkyl groups include 4-carboxyethylcapryl and 3-carboxymethyltoluyl. Amino-substituted groups include aminocaproyl, aminostearyl, aminohexyl, aminolauryl and diaminooctyl.

In addition to the foregoing aliphatic groups, groups containing hetero-atoms, such as oxygen, sulfur or nitrogen, in the chain may also be used. Examples of these radicals are ethers of the alkoxyalkyl type, including methoxyhexyl and ethoxydecyl. Alkylthioalkyl groups include methylthiododecyl groups. Primary, secondary and tertiary amines may also serve as the terminal portion of the hydrophobic group. These include diisopropylamino, methylaminohexyl, and aminodecyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumyl, 1,3,5-triethylphenyl, styryl, allylphenyl, diphenylmethyl, triphenylmethyl, tetraphenylmethyl, 1,3,5-triphenylphenyl. Nitro- and halo-substituted may be exemplified by chloronitrophenyl, chlorodinitrophenyl, dinitrotoluol, and trinitroxylyl.

Amine-substituted components include methylaminotoluyl, trimethylaminophenyl, diethylaminophenyl, aminomethylphenyl, diaminophenyl, ethoxyaminophenyl, chloroaminophenyl, bromoaminophenyl and phenylaminophenyl. Halo-substituted aryl groups include fluoro-, chloro-, bromo-, iodophenyl, chlorotoluyl, bromotoluyl, methoxybromophenyl, dimethylaminobromophenyl, trichlorophenyl, bromochlorophenyl and bromoiodophenyl.

Groups derived from aromatic carboxylic acids are also useful. These include methylcarboxylphenyl, dimethylaminocarboxyltoluyl, laurylcarboxyltoluyl, nitrocarboxyltoluyl, and aminocarboxylphenyl. Groups derived from substituted alkyl esters and amides of benzoic acid may also be used. These include aminocarboxylphenyl and methoxycarboxyphenyl.

Titanates wherein R' is an epoxy group include tall oil epoxides (a mixture of 6 to 22 carbon alkyl groups) containing an average of one epoxy group per molecule and glycidol ethers of lauryl or stearyl alcohol.

Substituted naphthyl groups include nitronaphthyl, chloronaphthyl, aminonaphthyl and carboxynaphthyl groups.

Illustrative of the compounds of the instant invention are: $OCH_2C(O)OTi(OSOC_6H_4NH_2)_2$; $OCH_2C(O)OTi(OSO_2C_6H_4C_{12}H_{25})(OSO_2C_6H_4NH_2)$; $OCH_2C(O)OTi[OP(O)(OC_8H_{17})_2]_2$; $OCH_2C(O)OTi(OC_6H_4C(CH_3)_2C_6H_5)_2$; $OCH_2C(O)OTi[OP(O)(OC_{12}H_{25})_2]_2$; $OCH_2C(O)OTi(OCOC_{70}H_{141})_2$; $OCH_2C(O)OTi(OC_6H_4NH_2)_2$; $OCH_2C(O)OTi[OP(O)(OC_6H_4C_8H_{17})_2]_2$; $OCH_2C(O)OTi[OCO(CH_2)_6(OSO_2)CH_3]_2$; $OCH_2C(O)OTi(OCOC_6H_4Cl)[OP(O)(OH)OP(O)(OCH_3)_2]$; $OCH_2C(O)OTi[(OC_6H_2(NO_2)_3]_2$; $OCH_2C(O)OTi(2-SC_{10}H_7)_2$; $OCH_2C(O)OTi(OSO_2C_6H_5)_2$; $OC_2H_4C(O)OTi(OCOC_{70}H_{141})_2$; $OC_2H_4C(O)OTi[OCOCH_2N(C_2H_4(OC_2H_4)_{12}OCH_2C_6H_4NO_2)_2]_2$; $OC_2H_4C(O)OTi(OCOC_{72}H_{141})(OCOCH=CH_2)$; $OC_2H_4C(O)OTi[OCOC(C_{22}H_{43})_3](OCOCH_2OC_2H_5)$; $OC_2H_4C(O)OTi[OCOC_6H_4CH_2OCH_2C_6H_3(C_{36}H_{73})_2]-(OCOC_{70}H_{141})$; $OC_2H_4C(O)OTi[-OCOC(CH_2C_{10}H_7)(C_{22}H_{43})_2][OCOCH(SC_6H_{11})_2]$; $OC_2H_4C(O)OTi[OCOC(CH_3)=CH_2]_2$; $OC_2H_4C(O)OTi(OCOCH_2NH_2)_2$; $OC_2H_4C(O)OTi(OCOCH_2OCH_3)(OCOCHClCH_3)$; $OC_2H_4C(O)OTi(OCOCCl_3)_2$; $OC_2H_4C(O)OTi(OCOCHBrCH_2Cl)(OCOC_6H_5)$; $OC_2H_4C(O)OTi(OCOCH_2CN[OCOCH_2N(CH_3)_2]$; $OC_2H_4C(O)OTi[OCO(CH_2)_{14}CH(CH_3)_2]-[OCOC(CH_3)=CH_2]$;

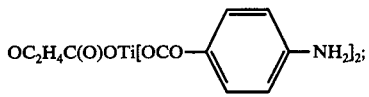

where $n$ is greater than 8 and less than 15; $OC_2H_4C(O)OTi[OCO(CH_2)_{14}CH(CH_3)_2]_2$; $OC_2H_4C(O)OTi[-OCO(CH_2)_{16}CH_3]_2$;

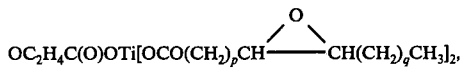

$OC_2H_4C(O)OTi[OCO(CH_2)_5NH_2]_2$; $OC_2H_4C(O)OTi[-OCOCH_2CH_2NH_2]_2$;

$OC_2H_4C(O)OTi[OCO(CH_2)_pCH\overset{O}{-\!\!\!-\!\!\!-}CH(CH_2)_qCH_3]_2$, where the sum of $p + q$ is more than 6 and less than 18; $OCH_2CH_2OTi[OP(O)(OC_8H_{17})_2]_2$; $OCH_2CH(CH_3)OTi[OP(O)(OC_{12}H_{25})_2]_2$; $OCH_2C(C_2H_5)_2OTi[OP(O)(OC_6H_4C_8H_{17})_2]_2$; $OC(CH_3)_2C(O)OTi[OC_6H_2(NO_2)_3]_2$; $OC_2H_4C(O)OTi[OP(O)(OH)OP(O)(OC_8H_{17})_2]_2$; $OC_2H_4C(O)OTi(OC_6H_4CH_3)_2$; $OC_2H_4C(O)OTi[OP(O)(OC_6H_5)_2]_2$; $OC_2H_4C(O)OTi(OSOC_{10}H_7)_2$; $OC_2H_4C(O)OTi(OSO_2C_6H_4Br)_2$; $OC_2H_4C(O)OTi[OP(O)(OC_6H_4NH_2)_2]_2$; and $OC_2H_4C(O)OTi(OC_6H_4NH_2)(OSO_2C_6H_5)$.

The organo-titanium chelates of the invention may be prepared by reacting the esters having the formula $(OR)_2Ti(A)_2$ with an equimolar amount of 2-hydroxypropionic acid or hydroxyacetic acid or their carbon substituted derivatives. In the case of the oxo derivatives (B = $R_2C$), the titanate ester is reacted with a 1,2- or a 1,3-glycol such as ethylene glycol or 1,3-butanediol.

The $(OR)_2Ti(A)_2$ compounds may be readily prepared as shown in the Freeport Sulphur Company U.S. Pat. Nos. 3,660,134, 3,697,494 and 3,697,495.

The inorganic materials may be particulate or fibrous and of varied shape or size, so long as the surfaces are reactive with the hydrolyzable group of the organo-titanium compound. Examples of inorganic reinforcing materials include metals, clay, carbon black, calcium carbonate, barium sulfate, silica, mica, glass and asbestos. Reactive inorganic materials include the metal oxides of zinc, magnesium, lead, and calcium and aluminum, iron filings and turnings, and sulfur. Examples of inorganic pigments include titanium dioxide, iron oxides, zinc chromate, ultramarine blue. As a practical matter, the particle size of the inorganic materials should not be greater than 1 mm, preferably from 0.1 micron to 500 micron.

It is imperative that the alkoxy titanium salt be properly admixed with the inorganic material to permit the surface of the latter to react sufficiently. The optimum amount of the alkoxy titanium salt to be used is dependent on the effect to be achieved, the available surface area of and the bonded water in the inorganic material.

Reaction is facilitated by admixing under the proper conditions. Optimum results depend on the properties of the alkoxy titanium salt, namely, whether it is a liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 170° to 230° C.; high density polyethylene from 200° to 245° C.; polystyrene from 230° to 260° C.; and polypropylene from 230° to 290° C. Temperatures for mixing other polymers are known to those skilled in the art and may be determined by reference to existing literature. A variety of mixing equipment may be used, e.g., two-roll mills, Banbury mixers, double concentric screws, counter or co-rotating twin screws and ZSK type of Werner and Pfaulder and Busse mixers.

When the organic titanate and the inorganic materials are dry-blended, thorough mixing and/or reaction is not readily achieved and the reaction may be substantially completed when the treated filler is admixed with the polymer. In this latter step, the organic titanate may also react with the polymeric material if one or more of the R' groups is reactive with the polymer.

The treated filler may be incorporated in any of the conventional polymeric materials, whether thermoplastic or thermosetting, whether rubber or plastic. These are disclosed in detail in the aforesaid Freeport Sulphur Co. patents, the disclosures of which are incorporated herein by reference. The amount of filler depends on the particular polymeric material, the filler and the property requirements of the finished product. Broadly, from 10 to 500 parts of filler may be used per 100 parts of polymer, preferably from 20 to 250 parts. The optimum amount may be readily determined by one skilled in the art.

While the compounds of the invention may be used with any one of the aforesaid fillers, it is particularly surprising that they remain extremely active even in the presence of large amounts of free water. For this reason, they may be used with wet process silica, soft or hard clays, talc, alluminum silicate, hydrated alumina and fiberglass. While it is not fully understood why the chelate compounds retain their activity, they are clearly superior to other titanates, such as described in the aforesaid Freeport Sulphur Co. patents, in the presence of moisture.

The following example is typical of the mode of preparation of the compounds of the invention.

Example A: Preparation of 2,2-dimethyl-3-oxy-3-phenylcaproyl acetyl dodecylbenzenesulfonyl titanate.

Charged to a stirred 1 liter reactor equipped with external heat/cooling, reflux/distillation and vacuum capabilities, is 1.0 mole of tetraisopropyl titanate. The unit is set for reflux at atmospheric pressure. Thereafter 1.0 mole of dodecylbenzenesulfonic acid is added over about one half hour, followed by 1.0 mole each of glacial acetic acid and 2,2-dimethyl-3-oxy-3-phenylcaproic acid sequentially, each over a half hour period. Limited heat evolution is observed upon the addition of each reagent. After the additions are completed, the reaction mixture is refluxed for one hour at atmospheric pressure. The reaction mixture is then cooled to below 50° C. and the by-product isopropanol removed by distillation in vacuo to a bottoms temperature of about 150° C. at 10 mm Hg. The volatilized isopropanol is recovered via trapping in a liquid nitrogen-cooled receiver. Recovery of isopropanol is about 3.7 moles, i.e., 90% of theory. A small amount of isopropyl acetate is also recovered. A yield of pasty white product in excess of 90% of theory is obtained as residue. Purification was effected by recrystallization from ligroin to form a white crystal (m.p. 87°–89° C.).

Example B: Preparation of di(dioctylphosphato) ethylene titanate.

Charged to a stirred 1 liter reactor equipped with external heat/cooling, reflux/distillation and vacuum capabilities, is 1.0 mole of tetraisopropyl titanate. The unit is set for reflux at atmospheric pressure. Thereafter 1.0 mole of ethylene glycol is added, followed by 2.0 moles of dioctyl, hydrogen phosphate, each over a half hour period. Limited heat evolution is observed upon the addition of each reagent. After the additions are completed, the reaction mixture is refluxed for one hour at atmospheric pressure. The reaction mixture is then cooled to below 50° C. and the by-product isopropanol removed by distillation in vacuo to a bottoms temperature of about 150° C. at 10 mm Hg. The volatilized isopropanol is recovered via trapping in a liquid nitrogen-cooled receiver. Recovery of isopropanol is about 3.7 moles, i.e., 90% of theory. A yield of pasty white product in excess of 90% of theory is obtained as residue. Purification was effected by recrystallization from ligroin to form a white crystal (m.p., 41°–43° C.).

Example C

Following the general procedure outlined above, additional compounds falling within the scope of the invention were prepared. The table below describes the particular compound by reference to the chelating ligand and the monovalent ligands (A and A') and sets forth a physical description, the melting point and the viscosity of the product:

Physical Properties of Selected Titanium Chelates
General formula $CTiA,A'$ where C is a chelating divalent ligand and A and A' are monovalent lingands.

| Chelating Ligand | Monovalent Ligand | | Physical Appearance | M.P., ° C. | Viscosity cps at 100° C. |
| --- | --- | --- | --- | --- | --- |
| | A | A' | | | |
| Ethylenedioxy | Isostearate | Isostearate | Red liquid | 3–10 | 180 |
| Ethylenedioxy | Isostearate | Methacrylate | Beige solid | 35–39 | 105 |

-continued

Physical Properties of Selected Titanium Chelates
General formula CTiA,A' where C is a chelating divalent ligand and A and A' are monovalent lingands.

| Chelating Ligand | Monovalent Ligand A | A' | Physical Appearance | M.P., °C. | Viscosity cps at 100° C. |
| --- | --- | --- | --- | --- | --- |
| Ethylenedioxy | Methacrylate | Methacrylate | Beige solid | 90–93 | 91 |
| Ethylenedioxy | Acrylate | Acrylate | Beige solid | Decomposes, 123–126 | — |
| Ethylenedioxy | Dioctylphosphate | Dioctylphosphate | Amber liquid | Below 0 | 286 |
| Ethylenedioxy | 4-aminobenzene-sulfonate | Dodecylbenzene-sulfonate | Grey powder | Decomposes, approx. 200 | — |
| Ethylenedioxy | Anthranilate | Anthranilate | Black powder | 93–98 | 1250 |
| Oxyacetate | Isostearate | Acrylate | Tan wax | 65–75 | 130 |
| Oxyacetate | Cumylphenolate | Cumylphenolate | Red powder | 83–86 | 330 |
| Oxyacetate | 2-formylphenolate | 2-formylphenolate | Black liquid | (wax) 12–16 | 610 |
| Oxyacetate | Isostearate | Isostearate | White wax | 32–39 | 410 |
| Oxyacetate | 4-aminobenzoate | Isostearate | Red powder | 69–72 | 320 |

In order to show the utility of the compounds of the invention, attention is directed to the following examples.

Example I

This example shows the importance of the chelate structure for viscosity control of wet silica in organic dispersions. A dispersion was made by blending 20 parts of a 0.8 micron wet process silica into a solution of 0.2 part of titanate in 80 parts of heavy mineral oil (flash point ca. 105° C.) in a Waring blender.

| Titanate | Mix Viscosity at 78° F. |
| --- | --- |
| None | 75,400 |
| Isopropyl triisostearoyl titanate | 21,800 |
| Isopropyl tri(dioctylphosphato)titanate | 23,500 |
| Isopropyl tri(dodecylbenzene-sulfonyl)titanate | 19,800 |
| 2-acetyl diisostearoyl titanate | 11,600 |
| 2-acetyl di(dioctyl-phosphato)titanate | 8,000 |
| 2-acetyl di(dodecylbenzene-sulfonyl)titanate | 9,400 |

The first three titanates set forth in the table, while effective a substantial viscosity reduction as compared to the control, are nonetheless substantially inferior to the three acetyl compounds at the end of the table. It is believed that this effect is realized because the compounds of the invention maintain their activity in the presence of the moisture present in the silica.

Example II

The effect of selected titanates on the tensile strength of 3 micron water washed clay and talc filled polypropylene in systems employing 50 wt. % filler and 0.5 wt. % of titanate is shown in the following table:

| Titanate | Tensile Strength, psi | |
| --- | --- | --- |
| | Clay | Talc |
| None | 3400 | 4200 |
| 2-acetyl diisostearoyl titanate | 3650 | 4400 |
| 2-acetyl di(dioctyl-phosphato)titanate | 4100 | 5000 |

This example shows the increased tensile strength in both the talc- and clay-filled polypropylene with two of the compounds of the invention.

Example III

The effect of selected titanates on the Dart Impact Strength of 50 wt. % water-washed 3 micron clay-filled Nylon 6 (Allied 8201) is shown. Filler was pretreated with 2 wt. % of titanate prior to incorporation into polymer matrix.

| Titanate | Flex Strength psi × 10³ | Dart Impact inch lb |
| --- | --- | --- |
| None | 15.2 | 3 |
| 2-acetyl 4-aminobenzene-sulfonyl dodecylbenzene sulfonyl titanate | 21.6 | 28 |
| 2-acetyl di(4-amino-benzoyl)titanate | 26.2 | 16 |
| 2-acetyl distearoyl titanate | 16.2 | 51 |

In each case the treated material has an improved flex strength and a marked improvement in impact strength.

gcl Example IV

The effect of selected titanates of the invention on the properties of 0.8 micron wet process silica filled polyurethane is shown in this example. The formulation contained 20 wt. % filled which was pretreated with 2.0 wt. % titanate prior to incorporation.

| Titanate | Tensile Strength psi | Elongation % |
| --- | --- | --- |
| None | 3100 | 330 |
| 2-acetyl di(2-hydroxy acetyl)titanate | 3950 | 270 |
| 2-acetyl di(dioctyl-phosphato)titanate | 3500 | 390 |
| 2-acetyl dimethacryl titanate | 3450 | 300 |
| 2-acetyl 4-aminobenzoyl isostearoyl titanate | 3900 | 300 |

All treated compounds show improved tensile strength as compared to the control. The phosphate derivative also shows increased elongation. The structure of the non-hydrolyzable A group is shown to be important in determining property improvements.

The chemical structure of the foregoing compounds was primarily determined by a consideration of the reactants involved and the by-products formed. In selected cases, elemental analysis, infrared analysis and analysis for free hydroxyl groups were performed. These verified the chemical structures postulated.

Example V

This example shows the effect of the titanate chelates on an unfilled epoxy. Two epoxy hardener mixtures were prepared, containing 80 parts of Epon 828 and 20 parts of an aliphatic amine curative, Celanese 874 hardener. To one of these freshly prepared samples was added 2 parts of 2-acetyl di(dodecylbenzenesulfonyl) titanate. Both of the mixtures were stirred for 2 minutes and their viscosity measured on a Brookfield viscosimeter. The results obtained are shown in the table below.

| Organo-titanium Compound | Brookfield Viscosity × 10³ cps |
| --- | --- |
| None | 3.9 |
| 2-acetyl di(dodecylbenzene-sulfonyl) titanate | 9.4 |

The above data show that the last composition has a substantially higher viscosity than the other sample.

Example VI

This example shows the use of ethylene di(dioctylphosphato) titanate to enhance the tinting effect of pigments in a water-based acrylic paint. The paint used was Rowe Products Inc. SRW3OX White and the pigment paste dispersion (Daniel Products Co. Tint-Ayd #WD-2228, Aqueous Tinting Color, Phthalo Blue) containing 32% pigments and 39% total solids. Ethylene di(dioctylphosphato) titanate was first mixed with the pigment to form blends containing 0.3%, 0.6%, 0.9%, 1.2% and 1.5% titanate based on the weight of the paste dispersion. To 100 parts of paint, 0.2 part of each of the treated paste dispersions was added. Observation showed, as compared to the control, even at the 0.3% level, that there was increased dispersion and flow. While increased tinting resulted in all cases, the enhancement of blue coloration was optimum with the 0.9% sample.

We claim:

1. An organo alpha, omega-alkylene titanate having the formula:

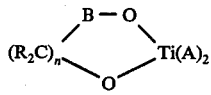

wherein A represents a non-hydrolyzable aroxy, thioaroxy, —OCOR', —OSO$_2$R", —OSOR", (R"O)$_2$-P(O)OP(OH)(O)—, or (R"O)$_2$P(O)O-group; B is an R$_2$C group or a carbonyl group; R is hydrogen or an alkyl group having from 1 to 6 carbon atoms; R' and R" are hydrogen or an alkyl, alkenyl, aryl, aralkyl or alkaryl group, or an alkyl, alkenyl, aryl, aralkyl, alkaryl, halo, amino, epoxy, ether, thioether, ester, cyano, carbonyl or aromatic nitro substituted derivative thereof; and $n$ is 1 or 2.

2. The compound of claim 1 wherein A is —OSO$_2$R" or a —OSOR" group and R" is phenyl, a substituted phenyl or an aralkyl group having from 5 to 24 carbon atoms in the alkyl chain.

3. The compound of claim 1 wherein A is a (R"O)$_2$-P(O)O— group and R" has from 6 to 24 carbon atoms.

4. The compound of claim 1 wherein A is a (R"O)$_2$-P(O)OP(OH)(O)— group and R" is an alkyl group having up to 12 carbon atoms.

5. The compound of claim 1 wherein R' is a long chain group having 18 carbon atoms.

6. The compound of claim 1 wherein the aryl portion of the aroxy and thioaroxy groups is phenyl or naphthyl.

7. The compound of claim 1 wherein the non-hydrolyzable groups are OCOR' having from 1 to 18 carbon atoms.

8. An organo-titanate compound having the formula:

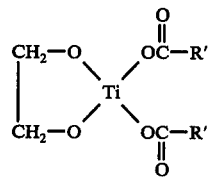

wherein R' is an isostearyl group.

9. An organo-titanate compound having the formula:

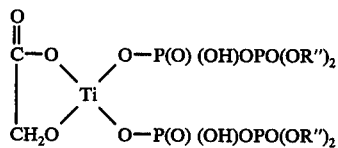

wherein R" is an octyl group.

10. An organo-titanate compound having the formula:

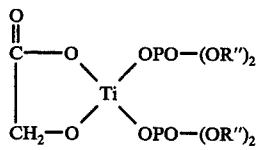

wherein R" is an octyl group.

11. An organo-titanate compound having the formula:

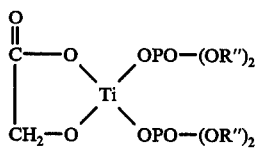

wherein R" is a dodecyl group.

12. An organo-titanate compound having the formula:

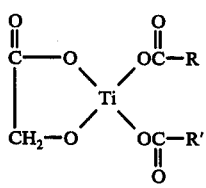

wherein R is an —CH=CH$_2$ group and R' is an isostearyl group.

13. An organo-titanate compound having the formula:

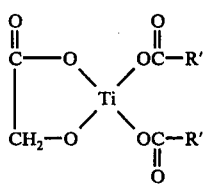

wherein R' is a methacryl group.

14. An organo-titanate compound having the formula:

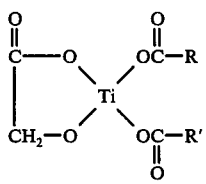

wherein R is an isostearyl group and R' is a 4-aminophenyl group.

15. An organo-titanate compound having the formula:

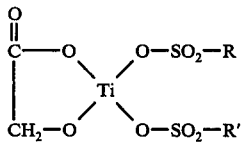

wherein R is a 4-aminophenyl group and R' is a dodecylphenyl group.

16. An organo-titanate compound having the formula:

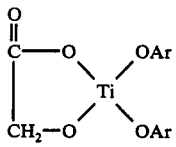

wherein Ar is a cumylphenyl group.

17. An organo-titanate compound having the formula:

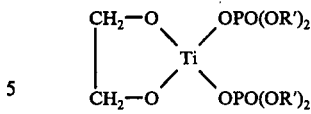

wherein R' is an octyl group.

18. An organo-titanate compound having the formula:

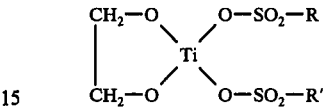

wherein R is a 4-aminophenyl group and R' is a dodecylphenyl group.

19. The composition of matter comprising comminuted inorganic material reacted with an alpha, omega-alkylene titanate having the formula:

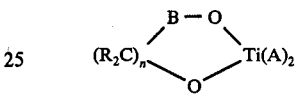

wherein A represents a non-hydrolyzable aroxy, thioaroxy, —OCOR', —OSO$_2$R", —OSOR", (R"O)$_2$P(O)OP(OH)(O)—, or (R"O)$_2$P(O)O— group; B is an R$_2$C group or a carbonyl group; R is hydrogen or an alkyl group having from 1 to 6 carbon atoms; R' and R" are hydrogen or an alkyl, alkenyl, aryl, aralkyl or alkaryl group, or an alkyl, alkenyl, aryl, aralkyl, alkaryl, halo, amino, epoxy, ether, thioether, ester, cyano, carbonyl, or aromatic nitro substituted derivative thereof; and $n$ is 1 or 2.

20. A filled polymeric composition which comprises a polymeric material admixed with a comminuted inorganic material reacted with an organic alpha, omega-alkylene titanate having the formula:

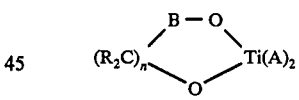

wherein A represents a non-hydrolyzable aroxy, thioaroxy, —OCOR', —OSO$_2$R", —OSOR", (R"O)$_2$P(O)OP(OH)(O)—, or (R"O)$_2$P(O)O— group; B is an R$_2$C group or a carbonyl group; R is hydrogen or an alkyl group having from 1 to 6 carbon atoms; R' and R" are hydrogen or an alkyl, alkenyl, aryl, aralkyl, or alkaryl group, or an alkyl, alkenyl, aryl, aralkyl, alkaryl, halo, amino, epoxy, ether, thioether, ester, cyano, carbonyl or aromatic nitro substituted derivative thereof; and $n$ is 1 or 2.

* * * * *